United States Patent [19]

Chan et al.

[11] Patent Number: 5,356,772

[45] Date of Patent: Oct. 18, 1994

[54] PROCESS FOR PREPARING AN IMPROVED WESTERN BLOT IMMUNOASSAY

[75] Inventors: Emerson W. Chan; William G. Robey, both of Libertyville; Werner Schulze, Waukegan, all of Ill.

[73] Assignee: Abbott Laboratories, Abbott Park, Ill.

[21] Appl. No.: 622,311

[22] Filed: Dec. 5, 1990

Related U.S. Application Data

[63] Continuation of Ser. No. 350,180, May 9, 1989, abandoned.

[51] Int. Cl.$^5$ .................... C12Q 1/70; C12P 19/38; G01N 33/53
[52] U.S. Cl. ..................... 435/5; 435/69.1; 435/974; 435/87; 436/548; 930/221
[58] Field of Search ............ 435/5, 87, 69.1, 974; 436/548; 930/221

[56] References Cited

U.S. PATENT DOCUMENTS

| | | | |
|---|---|---|---|
| 4,452,901 | 6/1984 | Gordon et al. | 436/506 |
| 4,843,011 | 6/1989 | Sarngadharan et al. | 436/548 |
| 4,980,279 | 12/1990 | Peters et al. | 436/87 |

FOREIGN PATENT DOCUMENTS

| | | |
|---|---|---|
| 8703965 | 7/1987 | PCT Int'l Appl. |
| 0063810 | 4/1982 | World Int. Prop. O. |
| 0173295 | 6/1985 | World Int. Prop. O. |

OTHER PUBLICATIONS

Beggar, et al Int. J. Cancer 35, 763–767, 1985.
Lin, et al J. Virology 59, 522–524, 1986.
Lee, et al J. Immunol. Methods 106, 27–30, 1988.
Immunochemistry in Practice Johnstone & Thorpe 2nd Ed, Blackwell Scientific Publications, 1987, p. 201.
Derer, et al., J. Allergy and Clin. Immunol., 74:85–92 (1984).

Primary Examiner—Margaret Parr
Assistant Examiner—Bradley L. Sisson
Attorney, Agent, or Firm—Lawrence S. Pope

[57] ABSTRACT

The present invention encompasses an improved immunoassay method which involves the simultaneous transfer of multiple antigens onto a single solid support. The antigens which may be utilized by this method may be either naturally or recombinantly produced and may be purified on a variety of electrophoresis gels. This method is particularly useful to provide an extremely sensitive multiple component assay using essentially pure antigenic polypeptides capable of detecting the presence or antibodies to HIV-1 or HIV-2 viruses in infected patients.

14 Claims, No Drawings

PROCESS FOR PREPARING AN IMPROVED WESTERN BLOT IMMUNOASSAY

This application is a continuation of application Ser. No. 07/350,180, filed May 9, 1989, abandoned.

FIELD OF THE INVENTION

This invention encompasses an improved immunoassay method which involves the simultaneous transfer of multiple antigens onto a single solid support. The antigens which can be utilized by this method can be either naturally or recombinantly produced and may be purified on a variety of electrophoresis gels. This method is particularly useful to provide an extremely sensitive multiple component assay using essentially pure antigenic polypeptides capable of detecting the presence of antibodies to HIV-1 or HIV-2 viruses in infected patients.

BACKGROUND OF THE INVENTION

The human immune system responds to viral infections by generating antibodies to various viral antigens. The number of antibodies and the amount of each different antibody produced depends on the virus and the virus antigen which initiates the antibody response.

Current immunoassay systems have proven useful to monitor viral infections. For example, it is possible to monitor HIV-1 or HIV-2 infections using immunoassays which use partially purified viral lysates. Unfortunately, these lysates may contain disproportionate quantities of various antigens or may lack important antigenic polypeptides. These deficiencies detrimentally affect both the sensitivity and selectivity of the assay. For HIV viruses, vital lysates may lack the transmembrane peptide, gp41, and the outer envelope protein, gp120.

Viral lysates are also unsatisfactory because they contain undesired immunologically reactive cellular components, antigenic aggregates and degraded antigenic fragments, as well as having antigenic peptides with differing degrees of glycosylation. These unavoidable extrinsic factors create purification problems when the viral lysates are separated on a gel because the resolution is less than ideal. Less than ideal resolution magnifies the separation difficulties caused by missing bands, diffused bands, overlapping nonspecific bands or too many bands and leads to unsatisfactory immunoblots that are difficult to interpret when the gel is transferred to an immunoblot surface. Furthermore, it is often difficult to prepare sufficient quantities of partially purified viral lysates for traditional immunoblots and the lack of sufficient quantities of a desired antigen increases the purification problems.

The problems associated with using viral lysates can be partially avoided by expressing desired antigenic polypeptides in various heterologous cell systems. These systems use recombinant techniques to insert virion genes of interest in cells that can produce quantities of these polypeptide products. This procedure often results in the production of the desired antigen in sufficient quantities, but is typically associated with the presence of new impurities and degraded antigenic fragments. Antigens produced by these methods may also form aggregates that must be minimized by using reducing agents or require the use of multiple gels to avoid both aggregation and degradation problems.

Traditional immunoblot methods lack the versatility to analyze multiple samples for reactivity with multiple antigens because of the need for many purification steps to provide antigens of a sufficient degree of homogeneity needed for selective and sensitive assays. The typical Western blot method is described by Gordon et al., U.S. Pat. No. 4,452,901 filed Mar. 18, 1980 issued Jun. 5, 1984. The document describes the procedures necessary to transfer antigenic peptides from a single gel to nitrocellulose. The present invention teaches the transfer of antigenic polypeptides from multiple gels.

The use of several antigens in a single assay has been described. Lin et al., J. Virol. 59:522–24 (1986) describes a dual antibody probing technique that permitted identification of Epstein-Barr virus and different herpes virus antigens in the same Western blot.

It is also possible to use multiple detection methods on a single Western blot. Lee et al., J. Immuno. Methods, 106:27–30 (1988) describes a technique which uses sequentially applied sets of probing antibodies, enzyme-conjugated developing antibodies and enzyme substrates to detect two or more types of interferon on a single Western blot. The same result can be achieved by simultaneously applying more than one type of probing antibody using a mixture of different enzyme-conjugated developing antibodies followed by successive applications of different substrates.

Gordon et al., European Patent Application Publication Number 0 063 810 published Mar. 11, 1982 describes immunoassay devices and kits made up of antigens or antibodies or both bound to a solid support. The use of the described solid supports makes possible a number of simultaneous antibody-antigen reactions in one operation. Gordon et al. describes applying single or successive doses of solutions of antigens or antibodies to the surface of the solid support using a pipet or syringe. In a preferred embodiment, the antigen is applied as a microdot formed by adding small volumes of an antigenic solution. The application does not describe immunoassays using antigens purified from a complex mixture of proteins.

Lefkovits, WO 87/03965, published Jul. 2, 1987, describes a test strip for several simultaneous assays. The test strip is made from nitrocellulose impregnated with an antibody that is cut into strips and mounted on an inert backing. Lefkovits describes soaking a support sheet in a solution of antigenic peptide and then cutting the sheet into strips but does not describe transferring the antigen to the solid support electrophoretically.

SUMMARY OF THE INVENTION

The present invention provides a method that permits the use of multiple recombinant and native antigens to simultaneous detect specific antibodies in the sera of infected patients and provides added versatility in the choice or use of particular antigens needed to provide maximized selectivity and sensitivity.

The present invention encompasses a method of detecting the presence of at least one biologically active substance in a sample by purifying more than one biologically active substrate from an impure mixture on a gel; separating a segment of said gel containing said purified substrate; selectively transferring said purified substrate from said gel segment to a solid support, wherein said active substrate is effectively attached to said solid support; contacting said active substrate bearing solid support with a sample containing at least one biologically active substance, wherein said active substance and said active substrate form a binding pair; and detecting the presence of said binding pair.

DETAILED DESCRIPTION OF THE INVENTION

This invention relates to a method of performing an improved Western blot assay that allows the use of combinations of antigens in various states of purity. These antigens may be conveniently and accurately used in immunoblot format to detect specific antibodies in solutions or body fluids. Although antigen preparations are generally available as complex mixtures, this invention provides a method that may be used to rapidly isolate single antigens and then present the antigens simultaneously to a solid support for immunoblot analysis free from impurities, aggregates or degraded fragments.

In a traditional Western blot, an antigenic mixture of interest is solubilized, usually with sodium dodecyl sulfate (SDS), urea, and, alternatively, with reducing agents such as 2-mercaptoethanol. Following solubilization, the material is separated on a polyacrylamide gel by electrophoresis and the antigens are then electrophoretically transferred to nitrocellulose paper, where they are bound irreversibly. This procedure is described by Gordon et al., U.S. Pat. No. 4,452,901 issued Jun. 5, 1984.

In the present invention, antigens are typically purified on various gels. The desired bands containing particular antigens are located and excised. The antigens in the excised gels are then electroblotted onto a solid support.

This improved Western blot offers advantages of superior sensitivity and specificity. These improvements may be accomplished by using increased amounts of purified antigens. An estimated amount of about 0.5 to 5.0 ug of antigen per excised band may be transferred onto a suitable solid support. Thus, sera that gives faint reactivities on traditional Western blots yields strong bands when practicing the present invention.

The electrophoretic transfer of the proteins gives a faithful replica of the arrangement of the excised gels on a suitable solid support. The antibody assays with such transferred electropherograms are carried out after the residual adsorption capacities of the solid support have been saturated by incubation with a non-specific protein. Immunoassays with electrophoretically transferred proteins are possible because no exchange takes place between the electrophoretically blotted specific proteins and the non-specific proteins used for blocking the residual binding sites of the support. The lack of interference of bound antigens with the non-specific proteins used for blocking the residual adsorption sites allows for prolonged incubation periods because further contact with the antisera and the indicator antibody do not generate side-reactions, such as exchange with the adsorbed non-specific proteins.

The solid support may be any material with sufficient surface porosity to allow access by detection antibodies and a suitable surface affinity to bid antigens. Microporous structures are generally preferred, but materials with gel structure in the hydrated state may be used as well. Useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers;

natural polymers containing nitrogen, such as proteins and derivatives, including cross-linked or modified gelatin;

natural hydrocarbon polymers, such as latex and rubber;

synthetic polymers which may be prepared with suitably porous structures, such as vinyl polymers, including polyethylene, polypropylene, polystyrene, polyvinylchloride, polyvinylacetate and its partially hydrolyzed derivatives, polyacrylates, polyacrylamides, polymethacrylates, copolymers and terpolymers of the above polycondensates, such as polyesters, polyamides, and other polymers, such as polyurethanes or polyepoxides;

porous inorganic materials such as sulfates or carbonates of alkaline earth metals and magnesium, including barium sulfate, calcium sulfate, calcium carbonate, magnesium carbonate, silicates of alkali and alkaline earth metals, aluminum and magnesium; and aluminum or silicon oxides or hydrates, such as clays, alumina, talc, kaolin, zeolite, silica gel, or glass (These materials may be used as fillers with the above polymeric materials); and mixtures or copolymers of the above classes, such as graft copolymers obtained by initiating polymerization of synthetic polymers on a pre-existing natural polymer.

All these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents which may be used in connection with this invention and is a preferred support material. Nylon also possess similar characteristics and is a suitable support material.

The solid support is preferably in the form of sheets of thickness from about 0.01 to 0.5 mm, preferably about 0.1 mm. The pore size may vary within wide limits, and is preferably from about 0.025 to 15 microns, especially from about 0.15 to 15 microns.

The surfaces of these supports may be activated by chemical processes which cause covalent linkage of the antigens or immunoglobulins to the support. The irreversible binding of the antigen or antibody is obtained, however, in general, by adsorption on the porous material by poorly understood hydrophobic forces. A preferred support based on nitrocellulose is sold under the tradename Millipore ® by the firm Millipore, Bedford, Mass., USA. Suitable supports are also described in U.S. patent application Ser. No. 7/227,272 filed Aug. 2, 1988 which is hereby incorporated by reference.

While the number of antigens that may be analyzed is limited only by the size of the support, their variety and composition are limitless. Antigens having similar sizes but isolated from different sources are possible because they may be transferred from different gels to different regions of the solid support. Reduction-sensitive or reduction-dependent antigens are conveniently handled by resolving them in separate preparative gels. In addition, the quantities of each antigen may be controlled and balanced to optimize assay selectivity and sensitivity.

Any desired number of antigens or combinations of antigens or immunoglobulins may be included in a single test procedure and then analyzed in a single operation. This invention may be used to monitor concentrations of antibodies which are normally endemic, but which may vary in a pathological situation, or to detect and quantitate antibodies which are only found in a pathological situation.

Once the selected antigens have been bound onto the solid porous support, the support must be processed to block excess binding sites of the porous material before being usable for the immunoassays. This is done by incubation of the support containing the antigenic polypeptides with non-specific proteins or with a mixture of such proteins, or with total serum, or any combination of these ingredients alone or together. The only limitation is that the proteins should not interfere or cross-react with any of the antibodies or antigens in the immunoassays, and that they be different from those mounted on the support.

The blocking of these residual adsorption sites may also be made in steps. Thus, in a preliminary step the support containing the fixed antigens or antibodies may be incubated with proteinaceous material. Such proteins are advantageously diluted in buffer and incubated with the support. After this preliminary treatment there may still be protein binding sites present which have not yet been completely blocked but which should be blocked before immunoassays have to be carried out. If there is background adsorption due to remaining binding sites or exchange of the non-specific protein, it may be prevented by carrying out the incubation with additional blocking agents. The presence of these mixtures both blocks remaining binding sites, and tends to prevent, by competition, exchange of the antibodies with proteins previously bound to non-specific sites or non-specific interaction of any kind with immunoglobulins.

In an immunoassay for the detection of antibodies the solid support is incubated with the sample diluted according to the expected antibody concentration, usually from about 1:100 to 1:10000 in blocking solution, for about 2 hours at room temperature or overnight at 4° C., and then washed with buffer to remove excess unbound antibodies. The support is then incubated with indicator antibody that is radioactively labelled, fluorescent, luminescent, conjugated with a fluorescent substance, or conjugated with an enzyme capable of giving a color reaction. The indicator antibody is usually diluted in a mixture of the blocking solution, incubated with the support for about two hours, and washed again in buffer.

All kinds of antibody-containing fluids of a patient, such as serum, plasma, cerebrospinal fluid, colostrum, lymphatic fluid, milk, saliva, urine, or stools may be analyzed using this invention.

The detection of the antigens on the support may be made with a suitable indicator antibody, or with a component of the complement system, or with a coupled enzyme system which is sensitive to the antigen-antibody reaction. This indicator antibody may also be any antibody which will react specifically with human or animal immunogobulins, or class specific antibodies which will react only with one desired antibody class such as IgG, IgM, IgA, IgD or IgE or any desired combination of such specific immunoglobulins.

The enzymes coupled with the indicator antibodies may be localized or quantitated by the formation of a radioactive, luminescent, or fluorescent product, a product with characteristic absorbance or reflection spectrum in the visible or outside The visible range, as long as the detecting reagent or reaction product remains localized at the site of the antigen-antibody complex. When a complement is used to detect the bound antigen-antibody complex, it may either be labelled in any one of the above ways, or be detected in turn by a specific anti-complement antibody.

The solid support, such as nitrocellulose sheets, obtained after application of the antigens may be dried and stored indefinitely at ambient temperature, provided it is maintained in a dehydrated state. The supports of the invention may also be stored after the blocking of residual adsorption bindings and, when dried, may be maintained indefinitely at low temperatures when protected from humidity.

In the method of this invention for immunological analysis, generally the support containing the antigens or immunoglobulins is contacted with the sample to be analyzed, for instance serum or plasma of an animal or human patient or person in routine health care, and dipped into a diluted solution or suspension of an indicator antibody directed against immunoglobulins of the animal species of the sample to be analyzed, and finally the bound second antibody is visualized. These steps are sufficiently simple and rapid, the entire operation may be performed within about three hours or less.

The group of antigens which may be used for carrying out immunological assays is very extensive and includes human biopsy material, mammalian tissue or cells, bodily fluids, mycoplasma, metazoan parasites, fungi, bacterial, protozoa, viruses, or preparations derived from any of these. Apart from the antigens described in the Examples, the following are also suitable. Viruses or antigens prepared from them such as influenza strains, including A, $A_1$, $A_2$, B, C, parainfluenze strains 1, 2 or 3, lymphocytic choriomeningitis virus, mumps, Q fever rickettsia, rabies, respiratory syncytial virus, Rotavirus, Rubella, Adenovirus, Epstein-Barr virus, Brucella, Hepatitis B, Cocksackie B1-B6, A9, Polio 1, 2 or 3, Reo, Echo 1-33; fungal antigens, such as *Histoplasmosa capsulatum, Coccidioides immitis, Blastomyces dermatitidis, Aspergillus fumigatus, flavus* or *carnea*; parasitic antigens, such as *Entemeba histolytica, Trypanosoma cruzi, Echinococcus granulosis, Schistosoma mansoni*; bacterial antigens, such as *Spirochete reiter, Treponema pallidum, Escherichia coli*, Leptospira, Listeria, Salmonella, Shigella, Staphylococci, Streptococci, *Legionella pneumophila*; auto-antigens, such as nuclear RNP, complement fractions, human serum proteins, rheumatoid factor, insulin, insulin receptor, thyroid stimulating hormone receptor, acetylcholine receptor and other hormones, receptors or allergens.

The present invention may also be used in the detection and monitoring of antigens of any kind, such as drugs and hormones. Such tests apply specific antibodies to a porous support, and detect and quantitate specific antigens by the inverse of the immunoassay procedures described above. The property of complement proteins to bind specifically to antigen-antibody complexes may then be used directly or indirectly to visualize and quantitate the specific antigens, such as drugs or other pharmacological reagents, or hormones, or any desired combination of such antigens.

The solid support may be stored and shipped in a dry state or after cutting off individual test strips perpendicular to the lines of the antigens. The strips may be as thin as is practicable, but generally not be more than 3 mm in width. For the actual test, all reagents may be readily stored in a lyophilized from in suitable aliquots, and reconstituted for the test.

The serum to be investigated is diluted by a suitable factor in saline containing blocking solution. Dilution factors of about 1:100 to 1:10000 cover most uses. The strip is immersed in one of these diluted solutions, for example, in a disposable well insert. The strips are incubated in this diluted solutions for about 2 hours at room temperature or overnight at 4° C. with gentle agitation. The excess serum is then washed out. The timing of the washes is not critical. The samples of the indicator antibody are then added. This is usually a dilution of peroxidase coupled goat anti-human IgG and the treatment continued for about 2 hours at room temperature. The dilution is also usually in blocking solution. The indicator antibody is then washed out. The indicator antibody is then visualized by an appropriate procedure, such as fluorescence, autoradiography or suitable substrate for the coupled enzyme. In the case of peroxidase, the substrate might be dianisidine or chloronaphthol in the presence of hydrogen peroxide. The color reaction is then allowed to develop, for about 30 minutes to 2 hours.

The method of this invention is not limited to antigen or antibody analysis. Macromolecular organic substances of animal or vegetable origin including proteins, protein conjugates, such as glycoproteins, lipo-proteins or protein-nucleic acid complexes may all be used as Long as they may be applied to solid supports.

This invention has versatile applications for immunodiagnostics of viral infections in general. By applying multiple specific antibodies on nitrocellulose strips instead of antigens, the process may be converted into a multiple antigen assay. Thus, the process may be used conveniently to provide key information on antigen and antibody serology important for the diagnosis and staging of an infection. In addition, combination tests may be set up to simultaneously monitor co-infections such as HIV-1 and HIV-2, or HIV-1 and HTLV-1, or HIV-1 and HBV, or HIV-1 and CMV.

EXAMPLES

The following examples are illustrative of specific embodiments of this invention and do not Limit the scope of the claims. Those skilled in the art will readily determine obvious variants of the following examples that are within the scope of the present invention.

EXAMPLE 1

3-Band Western Blot (3B-WB) for the Serodetection of HIV-1 Antibodies

An improved Western blot was designed for the detection of HIV antibodies using three specific antigens. This 3-band composite Western blot contains the key HIV env and core antigens: gp120, p41, and p24. Native gp120 was purified from HIV-1 infected H9 cells, and p41 and p24 were recombinant antigens produced and purified from $E.\ coli$. The 3 antigens (30–300 ug depending on purity) were each separately run on a 1.5 mm thick 12.5% SDS Laemmli polyacrylamide gel (12 cm × 16 cm) together with prestained markers on both sides. Electrophoresis was conducted at 45 v. at room temperature overnight (about 16 hours) until the dye front was near the bottom of the gel (about 11 cm from the origin). Gp120 was run under non-reducing conditions (no DTT) and p41 and p24 were run under reduced conditions (10 mM DTT).

The antigenic bands were located relative to the prestained protein markers and excised with a razor blade. The excised gel slices were laid onto a piece of cellulose nitrate and the antigens were transferred onto the cellulose nitrate in a transblot BioRad Cell® at 65 v., 0.2 Amps for 5 hours at room temperature. The antigen impregnated cellulose nitrate sheet was then washed 3×15 min with Buffer (20 mM Tris pH 7.5, 500 mM NaCl 0.5% Triton X-100) at room temperature with gentle mixing on a rotary shaker. It was then soaked for 2 hours at room temperature or 4° C. overnight in Blocking Solution I (1% gelatin, 1% casein hydrolysate and 0.01% thimerasol in buffer), washed, and resoaked in Blocking Solution II (10% Non-Fat-Dry-Milk, 0.01% thimerasol in buffer). After washing, the sheet was air-dried and cut perpendicularly to the bands into strips for immunoblots. The strips were stored at 4° C. until used. All washings were done 3 times in buffer with gentle mixing on a rotary shaker at room temperature for 5 minutes each.

To test sera for HIV specific antibodies, strips were reacted each with 4 ml samples of sera usually at 1:100 dilutions in Sample Buffer (20 mM Tris pH 7.5, 150 mM NaCl 0.5% Triton X-100, 0.1 mg/ml gentamicin, 0.1 mg/ml thimerasol, 10% goat serum, and 10% fetal calf serum) in tubes, or individual slots in a incubator tray, BioRad Catalog No. 170-4037. After incubation at 4° C. overnight samples were removed by aspiration, and strips were washed. The strips were then reacted with goat IgG-horseradish peroxidase conjugates specific for human IgG and IgM both at 1:1000 in Sample Buffer. After incubation at room temperature for 3 hours, the strips were washed and color was developed with a BioRad HRP Color Development Reagent using recommended conditions. The immunoblot strips were then photographed to record the presence or absence of antigenic bands.

The strips prepared according to the conditions described above yielded intense blue bands with known HIV positive human sera, and no bands with normal human sera. The specificity of the method is shown because mouse monoclonal antibodies specific for gp120, p41, and p24 each reacted only with its corresponding band. Mouse monoclonal antibodies specific for p18 and reverse transcriptase did not react. Furthermore, an antiserum prepared against $E.\ coli$ failed to detect $E.\ coli$ antigens on the strips.

The purity of the envelope antigens used in the above assay was shown by recovering the antigens in the excised bands of polyacrylamide gel by extraction with a phosphate buffered saline containing 0.1% triton. The recovered antigens were analyzed by SDS-PAGE. Silver staining of the gels showed that each antigen consisted of a single band of protein. Western blotting confirmed that these single bands were HIV specific and that there was an absence of smaller antigenic fragments that might indicate degradation.

EXAMPLE 2

Composite 5-Band Western Blot for the Serodetection of HIV-1, HIV-2, and HTLV-1 Antibodies A composite Western blot analogous to the Western blot of Example 1, above, was prepared for the detection of antibodies to HIV-1, HIV-2, and HTLV-1. This "combo" blot contained 5 antigens: gp120 of HIV-1; p41 of HIV-1; p24 of HIV-1; p41 of HIV-2 and; p21 of HTLV-1. The HIV-1 antigens were the same as described in Example 1. The HIV-2 and HTLV-1 were recombinant antigens derived from *E. coli*. These antigens were purified and then fractionated by preparative SDS/PAGE. The bands of antigen were located and excised from the gels. The antigens in the excised gel strips were electroblotted onto nitrocellulose together with the 3 antigens from HIV-1. Test strips were then prepared from the blotted sheet as described in Example 1.

The 5-band strips were tested with a panel of positive and negative control sera. The HIV-1 positive serum of this panel reached with the 3 HIV-1 bands only. The HIV-2 serum reacted with the p41 of HIV-2 and the p24 of HIV-1. This result was consistent with the known cross-reactivity between the p24 core antigens of the two HIV virus strains. The HTLV-1 serum reacted only with the p21 of HTLV-1. Two negative control sera did not react with any of the antigenic bands.

These results indicate the composite 5-band Western blot may detect HIV-1, HIV-2, and HTLV-1 positive sera with specificity.

EXAMPLE 3

Simultaneous Detection of HIV-1, HIV-2 and HTLV-1 Antibodies

The positive control sera of Example 2, above, were mixed at 1:1 ratios in various combinations and the mixtures were assayed with the 5-band test strips prepared according to Example 2. A mixture of HIV-1 and HIV-2 sera gave positive reactions with the bands containing gp120, p41, p24 of HIV-1 and p41 HIV-2 and no reactions with p21 HTLV-1. A mixture of HIV-1 and HTLV-1 sera gave positive reactions with the bands containing gp120, p41, and p24 of HIV-1, and p21 of HTLV-1, only. A mixture of HIV-2 and HTLV-1 sera gave positive reactions with the bands containing p24 HIV-1, p41 HIV-2 and p21 HTLV-1, only. A mixture of HIV-1, HIV-2 and HTLV-1 sera reacted with antigens contained in all 5 bands.

These results showed that each of the three types of vital antibodies, if present in a serum (such as by mixing in this case), may be detected specifically and simultaneously by the 5-band Western blot. It is likely that the 5-band test strips may also detect these antibodies in sera as a result of natural infections. Thus, the 5-band Western blot may be used for differential diagnosis of multiple infections.

COMPARATIVE EXPERIMENTS

Experiment 1—Simultaneous Titration of Antibodies of a Given HIV-1 Positive Serum to the 3 HIV Antigens The 3B-WB strip was used to simultaneously determine antibody titers of a HIV-1 positive serum, to the 3 antigens. Testing was conducted with 2-fold serial dilutions of the serum, and the results showed very strong titers to p41 and p24 (1:400,000) and a weaker titer to gp120 (1:1600).

These results showed the higher sensitivity of the 3B-WB relative to EIA and Western blot, and the capability of the 3B-WB to titrate antibodies to multiple antigens simultaneously.

Experiment 2—Monitoring Seroconversion

An 18 member serial-bleed seroconversion panel (Panel C, purchased from Boston Biomedica, Inc.) was tested by 3B-WB. Most EIA's register positivity starting on the 8th bleed. Standard vital based Western blot detected p24 antibodies as early as the 5th bleed. In comparison, 3B-WB yielded positive results for gp120, p41, and p24 antibodies beginning with the first bleed.

These data confirm the superior sensitivity of the 3B-WB relative to EIA and standard WB, and revealed the relative titers of the env versus core antibodies.

The adore panel was re-assayed and reached antibodies of the IgM type were monitored with a rabbit IgG-horse radish peroxidase conjugate specific for human IgM, Calbiochem Catalog No. 401875. The results showed a weak IgM response in five bleeds (3rd–7th). The IgM antibodies peaked at the 5th bleed, declined, and disappeared on the 8th bleed.

These data showed the versatility and sensitivity of the 3B-WB.

Experiment 3—Correlating Immune Status with Infectivity Status

Ten sera each from individuals at the 3 stages of infection (ASY, ARC, and AIDS) were evaluated by 3B-WB. Results showed that they all had p41 and gp120 antibodies, but the prevalence of p24 antibodies declined as the disease progressed.

These data are consistent with reported findings and demonstrated the importance of p41 as a marker for the serodetection of HIV infections.

Although the present invention has been described in terms of a preferred embodiment, it is understood the invention comprehends all embodiments within the scope of the following claims.

We claim:

1. A method of detecting the presence of at least one biologically active substance in a sample comprising:
    (a) purifying at least one antigenic reactive substrate on at least one gel from at least one impure mixture;
    (b) excising from each said gel at least one segment which contains at least one said purified substrate;
    (c) selectively transferring each said purified substrate from said segment to a solid support, wherein said purified substrate is effectively attached to said solid support;
    (d) contacting said purified substrate bearing solid support with a sample suspected of containing at least one immunologically active substance, wherein said active substance and said purified substrate form a binding pair; and
    (e) detecting the presence of said binding pair on said solid support.

wherein more than one segment containing said purified substrate is separated from the same gel.

2. The method of claim 1, wherein said solid support is nitrocellulose.

3. A method of detecting the presence of at least one biologically active substance in a sample comprising:
    (a) purifying at least one antigenic reactive substrate on at least one gel from at least one impure mixture;
    (b) excising from each said gel at least one segment which contains at least one said purified substrate;
    (c) selectively transferring each said purified substrate from said segment to a solid support, wherein said purified substrate is effectively attached to said solid support;
    (d) contacting said purified substrate bearing solid support with a sample suspected of containing at least one immunologically active substance, wherein said active substance and said purified substrate form a binding pair; and (e) detecting the presence of said binding pair on said solid support, wherein more than one segment containing said purified substrate is separated from more than one gel.

4. The method of claim 3, wherein said solid support is nitrocellulose.

5. A method of detecting the presence of at least one biologically active substance in a sample comprising;
   (a) purifying at least two antigenic reactive substrates on at least two gels frown at least one impure mixture;
   (b) excising from each said gel at least one segment which contains at least one said purified substrate;
   (c) selectively transferring each said purified substrate from said segment to a solid support, wherein said purified substrate is effectively attached to said solid support;
   (d) contacting said purified substrate bearing solid support with a sample suspected of containing at least one immunologically active substance, wherein said active substance and said purified substrate form a binding pair; and
   (e) detecting the presence of said binding pair on said solid support.

6. The method of claim 5 wherein at least two of said gels comprise one of reducing polyacrylamide and one of non-reducing polyacrylamide.

7. The method of claim 5, wherein said solid support is nitrocellulose.

8. A method of preparing a solid support capable of detecting the presence of at least one biologically active substance in a sample comprising;
   (a) purifying at least two antigenic reactive substrates on at least two gels from at least one impure mixture;
   (b) excising from each said gel at least one segment which contains at least one said purified substrate;
   (c) selectively transferring each said purified substrate from said segment to a solid support, wherein said purified substrate is effectively attached to said solid support.

9. The method of claim 8 wherein said active substance is an antibody.

10. The method of claim 8 wherein said reactive substrate is an antigen.

11. The method of claim 10 wherein said antigen is selected from the group consisting of HIV and HTLV antigens.

12. The method of claim 11 wherein said HIV and HTLV antigens are selected from the group consisting of HIV-1 gp120, HIV-1 p41, HIV-1 p24, HIV-2 p41 and HTLV-1 p21 antigens.

13. The method of claim 8 wherein the amount of said antigenic reactive substrate purified on said gel ranges from 0.5 to 5 micrograms.

14. The method of claim 8, wherein said solid support is nitrocellulose.

* * * * *